(12) United States Patent
Arai et al.

(10) Patent No.: US 6,383,818 B1
(45) Date of Patent: May 7, 2002

(54) METHOD OF ANALYZING BLOOD COMPONENT

(75) Inventors: Takaki Arai; Kenichiro Yazawa; Osamu Seshimoto, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/496,082

(22) Filed: Feb. 1, 2000

(30) Foreign Application Priority Data

Feb. 2, 1999 (JP) ............................................. 11-024479

(51) Int. Cl.$^7$ ................................................. G01N 1/00
(52) U.S. Cl. .................... 436/177; 73/863.23; 210/505; 210/739; 436/86
(58) Field of Search ........................... 436/71, 86, 170, 436/174, 177, 178; 210/505, 506, 767, 787, 806, 96.1, 739, 781; 73/1.01, 1.02, 1.03, 53.01, 61.41, 61.43, 64.56, 863.2; 700/266, 273; 494/37

(56) References Cited

U.S. PATENT DOCUMENTS

| | | | | |
|---|---|---|---|---|
| 4,810,394 A | * | 3/1989 | Masuda | ....................... 436/177 |
| 5,139,685 A | * | 8/1992 | De Castro et al. | .......... 436/177 |
| 5,460,777 A | * | 10/1995 | Kitajima et al. | ............. 436/170 |
| 5,876,605 A | * | 3/1999 | Kitajima et al. | ............. 436/177 |
| 6,045,699 A | * | 4/2000 | Yazawa et al. | .............. 436/178 |
| 6,225,130 B1 | * | 5/2001 | Kitajima et al. | ............. 436/177 |

* cited by examiner

Primary Examiner—Joseph W. Drodge
(74) Attorney, Agent, or Firm—Reed Smith LLP

(57) ABSTRACT

The present invention provides a method of analyzing a blood component by filtering blood using a glass fiber filter to obtain a plasma or serum sample and measuring the sample, wherein some plasma or serum samples obtained by using the same type glass fiber filter and by a standard method have previously been measured to determine a and b of the formula $$Y = ax + b$$

wherein Y is the analytical value obtained by the standard method and x is the analytical value obtained by using the glass fiber filter, and the analytical value of the blood is corrected by using the above formula.

6 Claims, 3 Drawing Sheets

METHOD OF ANALYZING BLOOD COMPONENT

BACKGROUND OF THE INVENTION

This invention relates to a method of correcting an analytical value of a plasma or serum sample obtained by filtering blood using a glass fiber filter.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filters have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter cartridge composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1).

Another blood filter cartridge composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

Incidentally, the electrolytes to be measured for clinical assay include calcium, sodium, potassium, chlorine and so on. However, as a result of investigating commercial glass fiber filters, the inventors found that some of them are eluted into blood to cause analytical errors.

They also found that analytical errors were caused by proteins, ammonia formed nitrogen, and enzymes, such as alkaline phosphatase.

SUMMARY OF THE INVENTION

An object of the invention is to provide an analytical method capable of removing an error caused by the filtration of blood using a glass fiber filter, and thereby to provide a simple method of analyzing a blood component.

The inventors investigated eagerly in order to solve the above problems, and found that, the errors caused by a glass fiber filter due to electrolytes, proteins, ammonia formed nitrogen, enzymes and the like are represented by a linear equation, and the errors generated by the same type of glass fiber filters are almost equal. Accordingly, the errors can be corrected by the linear equation of which two factors have previously been determined as to the analytical item to be measured.

The present invention has been made based on the above findings, and provides a method of analyzing a blood component by filtering blood using a glass fiber filter to obtain a plasma or serum sample and measuring the sample, wherein some plasma or serum samples obtained by using the same type glass fiber filter and by a standard method have previously been measured to determine a and b of the formula $$Y=ax+b$$

wherein Y is the analytical value obtained by the standard method and x is the analytical value obtained by using the glass fiber filter, and the analytical value of the blood is corrected by using the above formula.

Figure 1:
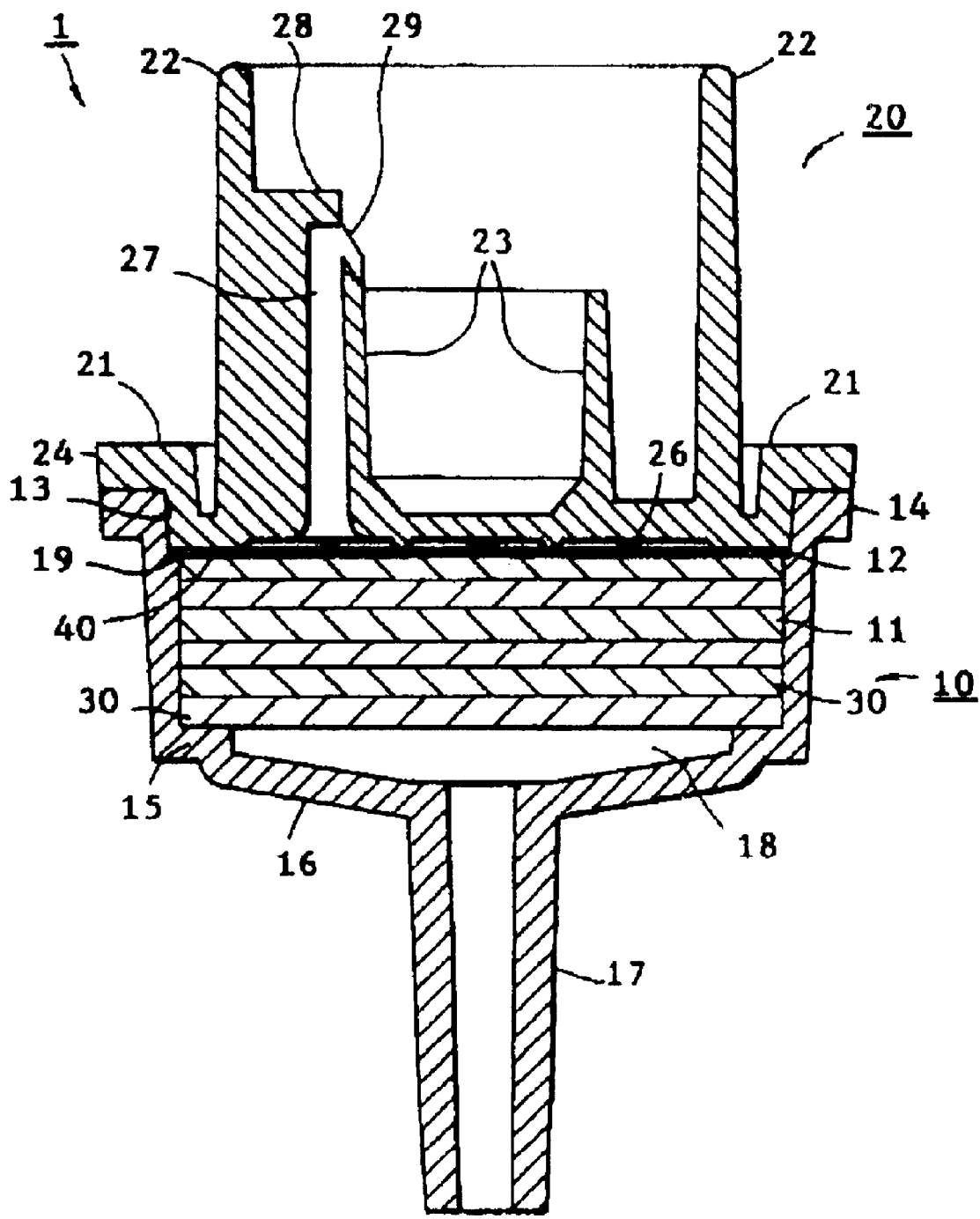
FIG. 1 is a longitudinal section of a blood filter cartridge used in the examples of the invention.

1 . . . Blood filter cartridge
10 . . . Holder body
11 . . . Glass fiber filter chamber (blood filter chamber)
12 . . . Microporous membrane chamber (blood filter chamber)
13 . . . Inclined portion
14 . . . Flange
15 . . . Fiber filter-placing portion
16 . . . Funnel-shaped disc portion
17 . . . Blood inlet
18 . . . Space
19 . . . Step portion
20 . . . Cap
21 . . . Outer wall
22 . . . Inner wall
23 . . . Cup
24 . . . Flange
25 . . . Rib
26 . . . Projection
27 . . . Filtrate passage
28 . . . Pent roof
29 . . . Filtrate outlet
30 . . . Glass fiber filter
40 . . . Polysulfone microporous membrane

DETAILED DESCRIPTION OF THE INVENTION

Preferable glass fiber filters have a density of about 0.02 to 0.5 g/cm$^3$, preferably about 0.03 to 0.2 g/cm$^3$, more preferably about 0.05 to 0.13 g/cm$^3$, and a retainable particle size of about 0.6 to 9 μm, preferably 1 to 5 μm. By treating the surface of a glass fiber with a hydrophilic polymer as disclosed in Japanese Patent KOKAI Nos. 2-208676, 4-208856, filtration proceeds faster and smoothly. Lectin or other reactive reagents or modifiers may be incorporated into a glass fiber, or a glass fiber may be treated therewith. Two or more glass fiber filters may be superimposed.

It is also possible that a glass fiber filter sheet is cut into small pieces, and packed in a holder. The thickness of a glass fiber filter sheet is about 0.2 to 3 mm, usually about 0.5 to 2 mm. The glass fiber filter sheet is cut into pieces having a diameter of about 10 to 30 mm, preferably about 15 to 25 mm. The shape of the piece is not limited, and may be square, rectangle, triangle disc or the like.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a define volume of water, and pressurizing or sucking at a constant pressure. The water permeation speed is filtrate volume per unit area and time, and is expressed by ml/sec.

For example, glass fiber filter 20 mm $\phi$ in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

Glass fiber filters particularly suitable for plasma or serum separation have a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

The blood filtering material used in the invention may be glass fiber filter alone or a combination of glass fiber filter and other blood filtering material(s). Another suitable blood filtering material is microporous membrane.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 $\mu$m or more, preferably about 0.3 to 5 $\mu$m, more preferably about 0.5 to 3 $\mu$m. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc.

Preferable microporous membranes are polysultone membrane, cellulose acetate membrane, and the like, and particularly preferred one is polysulfone membrane. In the blood filtering material of the invention, the glass fiber filter is located on the blood inlet side and the microporous membrane is located on the filtrate outlet side. The most preferable blood filtering material is a combination of the glass fiber filter and polysulfone membrane laminated in this order from the blood inlet side.

A suitable thickness of the glass fiber filter varies according to the plasma volume to be recovered and density (void content) and area of the glass fiber filter. A necessary amount of plasma for analyzing plural items using dry analytical elements is 100 to 500 $\mu$l. In practical viewpoint, a glass fiber filter having a density of about 0.02 to 0.2 g/cm$^3$ and an area of 1 to 5 cm$^2$ is suitable. In this case, a suitable thickness of the glass fiber filter layer is about 1 to 10 mm, preferably about 2 to 8 mm, more preferably about 4 to 6 mm. The above thickness can be made by superposing 2 to 10 sheets, preferably 3 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

Respective layers may be integrated by joining each other using partially disposed (e.g. spots) adhesive, according to disclosures in Japanese Patent KOKAI Nos. 62-138756-8, 2-105043, 3-16651, etc.

The blood filtering material is placed in a holder having a blood inlet and a plasma outlet. The holder is, in general, formed of a body containing the blood filtering material and a cap, and each of them is provided with at least one aperture. One is used as the blood inlet, and the other is used as the filtrate outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2 ml, especially about 0.7 to 1.5 ml.

Besides, it is preferable that the periphery of the blood filtering material is closely fitted to the wall of the filter chamber so as not to form a bypass of whole blood without a passing the filtering material.

The blood filter cartridge is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

The blood filter cartridge of the invention may be provided with a filtrate receiver. The filtrate receiver is connected to the filtrate outlet through a wall, and the filtrate outlet is located above the liquid level of the filtrate receiver. The filtrate outlet may be provided on the upper part of the side wall of the filtrate receiver or a pipe standing on the inside of the filtrate receiver. The filtrate receiver is made into various shapes in connection with various factors, such as the relation to the position of sucking analytical sample, the relation to the blood filtering chamber, the relation to optional other parts, and the like, and, in general, cylindrical or square. The bottom of the filtrate receiver is flat, funnel-shaped, round or the like. The volume of the filtrate receiver is, in the case of preparation of analytical sample for dry analysis, about 100 to 900 $\mu$l, usually about 200 to 600 $\mu$l, and has a depth of about 3 to 12 mm and a width (diameter a side length) of about 5 to 11 mm. As to the position of the position of the filtrate outlet, the underside of the filtrate outlet is located higher than the designed liquid level of the filtrate receiver by about 0.5 to 5 mm, usually about 1 to 2 mm. Although the volume of filtrate varies according to the hematocrit value of blood, the designed liquid level is of filtering blood having a hematocrit value of 20 to 60%. The filtrate receiver may be integrated with or separated from the holder.

The glass fiber filter used for the determination of the factors of the formula Y=ax+b is in the same type as that used for the filtration of blood to be measured. It is possible to vary the factors in the above formula by the type, brand, manufacturer, raw material, production, structure, properties, etc. of the glass fiber filter. On the other hand, when the glass fiber filter is of the same brand, particularly produced from the same raw material by the same method and apparatus, the factors become almost the same. Especially, the same lot product gives the same factors. Thereupon, according to analytical accuracy required, the factors a and b have previously been determined of the same brand, in the case of requiring high accuracy, the same lot, and the correction of an analytical value of a plasma a serum sample can be carried out by using the a, b values. In many cases, since a is 1, it is enough to determine only b in practical viewpoint. In the case that the blood filtering material is a combination of glass fiber filter and other filtering material(s), the factors a and b are preferably determined as to the combination of the glass fiber filter and other filtering material(s).

The standard method of blood separation, which is necessary for the determination of a and b, does not influence the concentration of an analytical object by the separation, i.e. denaturation and concentration variation of the analytical object can be neglected, and an actual means is centrifugation.

The a and b can be determined by measuring the concentration of an analytical object of plasma or serum having various concentrations of the analytical object separated by the glass fiber filter and by the standard method. It is preferable to select blood samples so as to cover the whole range of measurement, and in practical viewpoint, so as to cover 50% or more, preferably 80% or more of the measuring range. The number of blood samples is 2 at the minimum, and the greater the number is the more preferable. An actual number is about 5 to 10. The determination of a and b in the case of three or more blood samples is wellknown. For example, three whole blood samples are prepared having a concentration around the lower limit, the center and the upper limit of the measuring range, respectively. A half of each sample is centrifuged, and each supernatant is measured to obtain $Y_1$, $Y_2$ and $Y_3$ as the measured values. The other half of each sample is filtered by the glass fiber filter to be used, and each plasma (or serum) is measured to obtain $X_1$, $X_2$ and $X_3$ as the measured values. Using the above measured values, the a and b values of Y=ax+b are determined by the method of least squares.

Although the method of the invention can be applied to dry analysis and wet analysis, it is particularly suitable for the dry analysis using a dry analytical element.

The fundamental structure of dry analytical element is composed of a porous spreading layer, a hydrophilic polymer layer and a water-impermeable support laminated in this order.

The porous spreading layer has a function to spread components contained in an aqueous liquid sample in plane without uneven distribution and to supply them to the hydrophilic polymer layer at a constant rate per an unit area, and can be composed of every nonfibrous or fibrous porous material known for the spreading layer of conventional dry analytical elements. Examples of the spreading layer include nonporous isotropic microporous medium layers represented by membrane filter (blushed polymer) disclosed in U.S. Pat. No. 3,992,158, nonfibrous porous layers represented by continuous space-containing three dimensional lattice grain structure layer where polymer particulates are joined at spots by a water-nonwelling adhesive disclosed in U.S. Pat. No. 4,258,001, porous layers composed of woven fabric disclosed in U.S. Pat. No. 4,292,272, GB 2,087,074A, etc., porous layers composed of knitted fabric disclosed in EP 0.162,302A.

As porous membranes composed of thermoplastic material, there are porous membranes of cellulose derivatives, such as cellulose diacetate (DAC), cellulose triacetate (TAC), nitrocellulose (NC), hydroxymethyl cellulose (HMC) and hydroxyethyl cellulose (HEC), porous membranes of ethylene polymer and copolymers, such as polyethylene, polypropylene, polystyrene and polyvinyl chloride, porous membranes of polyethylene terephthalate, polycarbonate, polysulfone and the like, porous membranes of vinyl polymers and copolymers of acrylic acid, methacrylic acid and esters thereof, and the like. On the other hand, as porous membranes of not thermoplastic material applicable to the invention, there are porous membranes of condensation polymers, such as nylon, polyamide and polyurethane, porous membranes formed by joining inorganic material particulates, such as glass particulates and diatomaceous earth, using a small amount of polymer, porous membranes made of polyetrafluoroethylene, filter paper, glass fiber filter paper, and the like.

The spreading layer can be composed of two or more microporous layers as disclosed in EP 0,166,365A, EP 0,226,465A, etc.

The spreading layer can contain a nonionic, anionic, cationic or ampholytic surfactant in order to accelerate spreading of a sample. Besides, it can contain a spreading controller, such as hydrophilic polymer for the purpose of controlling spreading. Furthermore, it can contain all or a part of various reagents for accelerating the object detecting reaction or reducing or inhibiting interfering reactions.

A suitable thickness of the spreading layer is 20 to 200 $\mu$m, preferably 50 to 170 $\mu$m, more preferably 80 to 150 $\mu$m.

The hydrophilic polymer layer, in general, contains at least a part of reagents necessary for analysis, and in this case, the layer is called a reagent layer. The base material of the hydrophilic polymer layer is composed of one or more of various known polymers which are water-soluble, swellable or hydrophilic and are used for conventional dry analytical elements. The hydrophilic polymer is generally a natural or synthetic hydrophilic polymer having a swelling ratio in the range of about 1.5 to about 20 times, preferably from about 2.5 to about 15 times, at a water absorption at 30° C. Examples of the hydrophilic polymer are gelatins, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone. Instead of the hydrophilic polymer layer, a porous polymer membrane having a hydrophilic surface can be used.

A suitable thickness of the hydrophilic polymer layer is about 1 to 100 μm, preferably about 3 to 50 μm, more preferably about 5 to 30 μm. It is preferred that the hydrophilic layer is substantially transparent. The hydrophilic polymer layer can contain all or a part of various reagents for accelerating the object detecting reaction or reducing or inhibiting interfering reactions.

The water-impermeable support can be a known water-impermeable support used in conventional dry analytical elements, and includes a transparent film made of polyethylene terephthalate, polycarbonate of bisphenol A, polystyrene, cellulose ester, such as, cellulose diacetate, cellulose triacetate or cellulose acetate propionate, or the like. The thickness of the support is usually in the range of about 50 μm to 1 mm, preferably from about 80 μm to 300 μm. The support is usually light-transmissive, but in the case of measuring from the spreading layer side, it may be colored or may be opaque. The support can be provided with an undercoating layer or an adhesive layer on its surface to strengthen the adhesion of the hydrophilic polymer layer.

Various other layers may be incorporated into the dry analytical element according to analytical items or the like. Examples of the layers are a registration layer, a water absorption layer, a light-reflecting layer, a light-shielding layer, and the like.

Although a dry analytical element generally contains all reagents necessary for analysis, the dry analytical element of the invention includes that not containing a part or all of the reagents which will be supplied upon analysis which has been developed by the inventors.

It is preferable to input the above factors a and b into a computer which controls an analyzer, to print a bar code onto the frame of a dry analytical element which will be read by a bar code reader, to record magnetically onto a card issuance machine which will be read by a card reader of an analyzer, thereby to correct analytical values automatically.

EXAMPLES

Example 1

Figure 2:
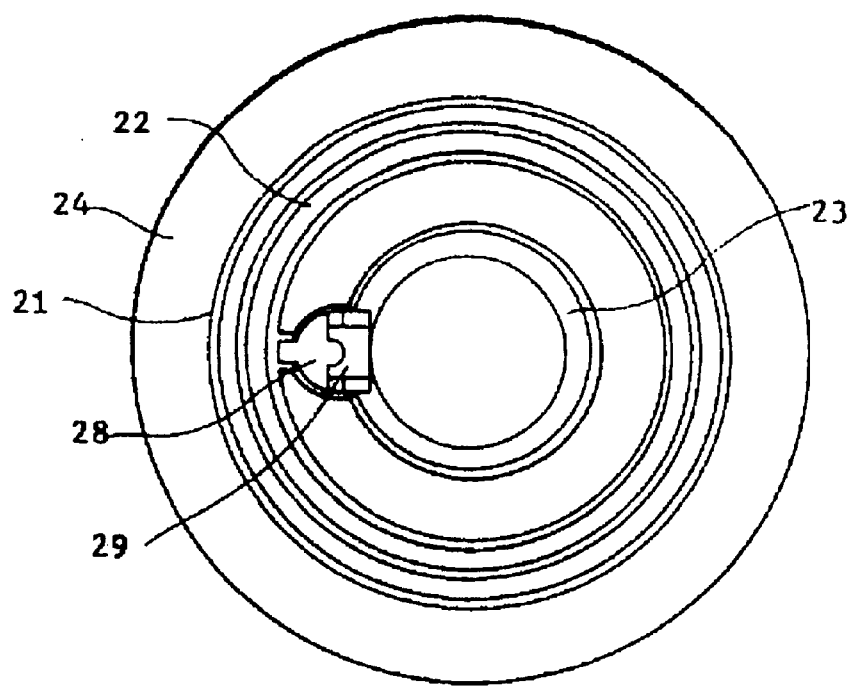
FIG. 2 is a plan view of the cap of the cartridge.
Figure 3:
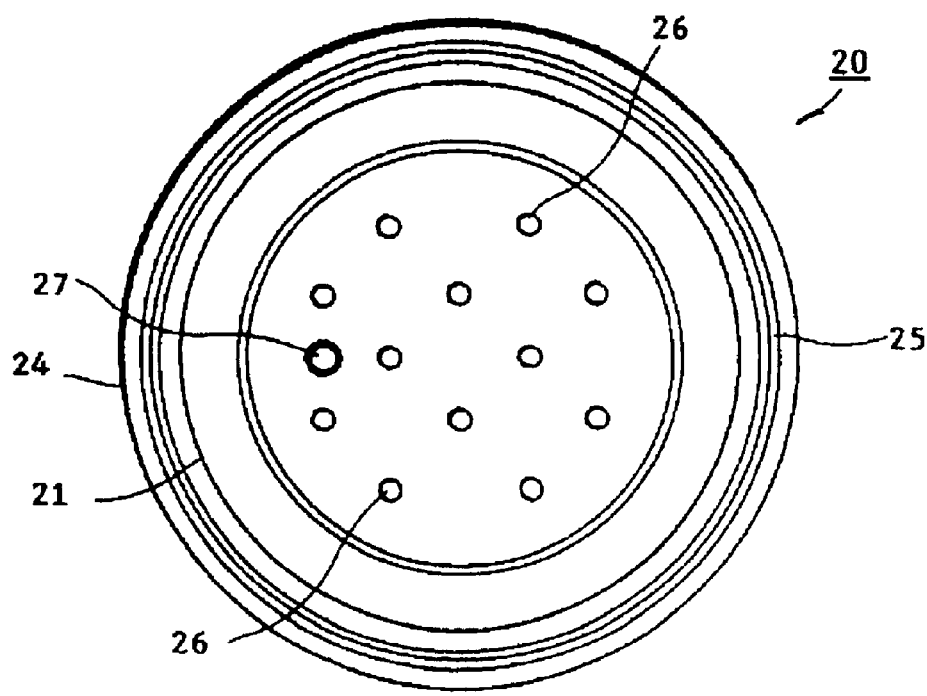
FIG. 3 is a bottom view thereof.

A blood filter cartridge illustrated in FIGS. 1–3 was prepared. The blood filter cartridge is, as shown in FIG. 1, composed of a holder 1 consisting of a holder body 10 and a cap 20 and blood filtering material consisting of a glass fiber filter 30 and a microporous membrane 40.

The holder body 10 is made of high-impact polystyrene resin, and has a glass fiber filter chamber 11 for containing the glass fiber filter 30 and a microporous membrane chamber 12 for containing a polysulfone microporous membrane as the microporous membrane 40 above the glass fiber filter chamber 11. The microporous membrane chamber 12 has a diameter greater than the glass fiber filter chamber, and the periphery of the microporous membrane 40 is nipped by the step portion 19 formed on the boundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber filter 30 from the bottom and forms a space 18 for spreading the liquid to be filtered over the whole surface of the glass fiber filter 30.

The cap 20 has an outer wall 21 and an inner wall 22 formed concentrically and a filtrate receiver 23 for storing the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined portion 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 40 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIG. 2, and the periphery of the large half circle conforms to the periphery of the filtrate passage 27. The filtrate outlet 29 of the filtrate is provide obliquely at the upper end of the filtrate passage 27, and has the form of a lower half ellipse. As shown in FIG. 2, screens (opposite faces) are formed on both sides from the filtrate outlet 29 to the upper edge of the filtrate receiver 23 in order to prevent scattering of filtrate.

The above blood filter cartridge has a diameter of the glass fiber filter chamber 11 of 20. 1 mm and a depth thereof of 5.9 mm, a thickness of the peripheral wall of the holder body of 2 mm, a width of each circumferential groove of 1.5 mm, a depth thereof of 1.5 mm and a thickness of the deepest portion thereof of 0.5 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the filtrate receiver 23 of 7.5 mm. The glass fiber filter 30 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm. The filtrate outlet 29 has a longitudinal diameter of 1.3 mm and a lateral diameter of 1.2 mm.

Using the above blood filter cartridge, the following tests were carried out.

Each 5 ml blood was drawn from 5 person in total of men and women by a vacuum blood collecting tube ("Venoject II, VP-H050", Termo) with heparin Na, and homogenized by turning 4 to 5 times gently.

Using a commercial 2 ml dropping pipette, each 2 ml of blood was pipetted into a 2 ml centrifuge tube, and centrifuged by a centrifuge ("CFM-200", Iwaki Glass) at 12,000 rpm for 3 minutes to separate plasma, and 200 μl of the plasma was collected rapidly into a A/T sample cup (EA-06T).

Na concentration and Cl concentration of the plasma were measured by an A/T measuring device, and $Y_{Na}$, $Y_{Cl}$ values were obtained.

The remaining 3 ml blood was filtered using the aforementioned blood filter cartridge to collect 350 μl plasma. Na concentration and Cl concentration of the plasma were measured by the A/T measuring device, and $X_{Na}$, $X_{Cl}$ values were obtained.

The results are summarized in Table 1.

TABLE 1

|    |   | Filtered (meq/L) | Centrifuged (meq/L) | Separation |
|----|---|------------------|---------------------|------------|
| Na | 1 | 143.2            | 140.0               | 3.2        |
|    | 2 | 144.3            | 141.5               | 2.8        |
|    | 3 | 145.5            | 142.0               | 3.5        |
|    | 4 | 143.5            | 140.5               | 3.0        |
|    | 5 | 143.2            | 139.5               | 3.7        |
|    |   | X = 143.9        | Y = 140.7           | 3.2        |
| Cl | 1 | 109.4            | 106.4               | 3.0        |
|    | 2 | 106.0            | 104.0               | 2.0        |
|    | 3 | 111.0            | 109.0               | 2.1        |
|    | 4 | 106.0            | 105.0               | 1.0        |
|    | 5 | 118.3            | 105.8               | 2.5        |
|    |   | X = 108.2        | Y = 106.0           | 2.2        |

The numeral in the lowest column of the separation corresponds to the factor b (a≈1) of the formula Y=aX+b, and is the correction shown in the following formula.

Correction of Na $X_{Na} - Y_{Na}$ = Correction of Na (meq/L)

Correction of Cl $X_{Cl} - Y_{Cl}$ = Correction of Cl (meq/L)

Subsequently, confirmation of the correction was carried out.

Using the aforementioned blood filter cartridge, 3 ml blood was filtered to obtain 350 μl plasma. The plasma was measured by an electrolyte analytical element ("Na—K—Cl", Fuji Photo Film Co., Ltd.) and an analyzer therefore ("Fuji Dri Chem, FDC-800", Fuji Photo Film Co., Ltd.).

Uncorrected Measured Value:

Measured values ($A_{Na}$ (meq/L)) were obtained without varying the built-in operator.

Corrected Measured Value:

The above correction was introduced into the built-in operator, and thereafter, measured values ($B_{Na}$ (meq/L)) were obtained.

The results are summarized in Table 2.

TABLE 2

| Sample      |   | Na         | CL         |
|-------------|---|------------|------------|
| Uncorrected | 1 | 143.3      | 109.6      |
|             | 2 | 144.5      | 111.6      |
|             | 3 | 144.4      | 108.6      |
|             | 4 | 143.7      | 108.7      |
|             | 5 | 144.6      | 108.5      |
|             |   | 144.5      | 109.4      |
| Corrected   | 1 | 142.0      | 107.7      |
|             | 2 | 140.8      | 106.2      |
|             | 3 | 141.8      | 106.9      |
|             | 4 | 141.0      | 107.2      |
|             | 5 | 141.4      | 107.5      |
| B           |   | 141.4      | 107.1      |
| A-B         |   | 3.1 (meq/L)| 2.3 (meq/L)|

Found corrections were

|    | A-B | Calc. |
|----|-----|-------|
| Na | 3.1 | 3.2   |
| Cl | 2.3 | 2.2   |

Example 2

Using the same blood filter cartridge and centrifuge, 50 blood samples of outpatients of a hospital were separated to obtain plasmas.

The plasmas were measured by a total protein analytical element ("TP-P", Fuji Photo Film Co., Ltd.) and an analyzer therefore ("Fuji Dri Chem, FDC-5000", Fuji Photo Film Co., Ltd.).

The results are summarized in Table 3.

TABLE 3

|        |     |      | TP       |            | Δ = Filtered- |
|--------|-----|------|----------|------------|---------------|
| Sample | Sex | Hct  | Filtered | Centrifuged| Centrifuged   |
| 1      | M   | 42.4 | 7.50     | 7.70       | −0.20         |
| 2      | F   | 37.2 | 7.35     | 7.45       | −1.10         |
| 3      | M   | 40.7 | 7.85     | 8.05       | −0.20         |
| 4      | M   | 43.5 | 7.60     | 7.70       | −0.10         |
| 5      | F   | 39.8 | 8.70     | 8.95       | −0.25         |
| 6      | F   | 39.7 | 7.25     | 7.55       | −0.30         |
| 7      | M   | 42.4 | 8.05     | 8.35       | −0.30         |
| 8      | M   | 45.1 | 7.65     | 7.80       | −0.15         |
| 9      | F   | 37.2 | 7.15     | 7.40       | −0.25         |
| 10     | M   | 42.2 | 7.50     | 7.80       | −0.30         |
| 11     | M   | 42.3 | 8.20     | 8.35       | −0.15         |
| 12     | F   | 40.1 | 8.35     | 8.50       | −0.15         |
| 13     | M   | 45.0 | 7.45     | 7.70       | −0.25         |
| 14     | F   | 36.7 | 7.55     | 7.75       | −0.20         |
| 15     | F   | 46.0 | 7.25     | 7.45       | −0.20         |
| 16     | F   | 40.4 | 8.60     | 8.85       | −0.25         |
| 17     | M   | 44.2 | 7.95     | 8.10       | −0.15         |
| 18     | M   | 41.1 | 7.85     | 8.05       | −0.20         |
| 19     | F   | 37.8 | 7.00     | 7.25       | −0.25         |
| 20     | M   | 44.1 | 7.75     | 8.05       | −0.30         |
| 21     | F   | 39.9 | 8.40     | 8.65       | −0.25         |
| 22     | M   | 48.1 | 7.95     | 8.25       | −0.30         |
| 23     | M   | 40.1 | 7.30     | 7.60       | −0.30         |
| 24     | M   | 19.0 | 7.05     | 7.25       | −0.20         |
| 25     | F   | 42.4 | 7.60     | 7.85       | −0.25         |
| 27     | M   | 39.3 | 7.80     | 7.95       | −0.15         |
| 28     | F   | 37.4 | 7.90     | 8.10       | −0.20         |
| 29     | M   | 41.4 | 7.85     | 8.20       | −0.35         |
| 30     | M   | 28.0 | 6.90     | 7.10       | −0.20         |

TABLE 3-continued

| | | | TP | | Δ = Filtered- |
|---|---|---|---|---|---|
| Sample | Sex | Hct | Filtered | Centrifuged | Centrifuged |
| 31 | F | 39.4 | 8.20 | 8.45 | −0.25 |
| 32 | M | 36.8 | 9.50 | 9.65 | −0.15 |
| 34 | F | 38.9 | 7.90 | 8.15 | −0.25 |
| 35 | M | 41.6 | 7.55 | 7.90 | −0.35 |
| 37 | M | 48.5 | 7.55 | 7.70 | −0.15 |
| 41 | M | 48.8 | 7.90 | 8.10 | −0.20 |
| 42 | F | 40.7 | 8.10 | 8.30 | −0.20 |
| 43 | M | 46.6 | 7.80 | 8.10 | −0.30 |
| 46 | M | 40.7 | 8.20 | 8.30 | −0.10 |
| 47 | M | 45.4 | 7.05 | 7.30 | −0.25 |
| 48 | M | 38.4 | 7.15 | 7.30 | −0.15 |
| 49 | M | 41.8 | 7.55 | 7.90 | −0.35 |
| 50 | M | 47.0 | 7.55 | 7.70 | −0.20 |
| Average | | | 7.74 | 7.97 | −0.223 |
| SD | | | 0.51 | 0.51 | 0.07 |
| Correlation | | | | 0.07 | |
| | | | | 0.9911 | |

The average correction value of a biochemical analytical item TP was −0.223 obtained from the data in Table 3. A correction formula was prepared by using respective measured values of the 50 plasmas obtained by centrifuging to which correction value was added and measured values of the 50 plasmas obtained by filtration. The correction formula directed to TP measurement of unknown whole blood samples thus obtained was $$Y = 0.9839X + 0.3475$$

Figure 4:
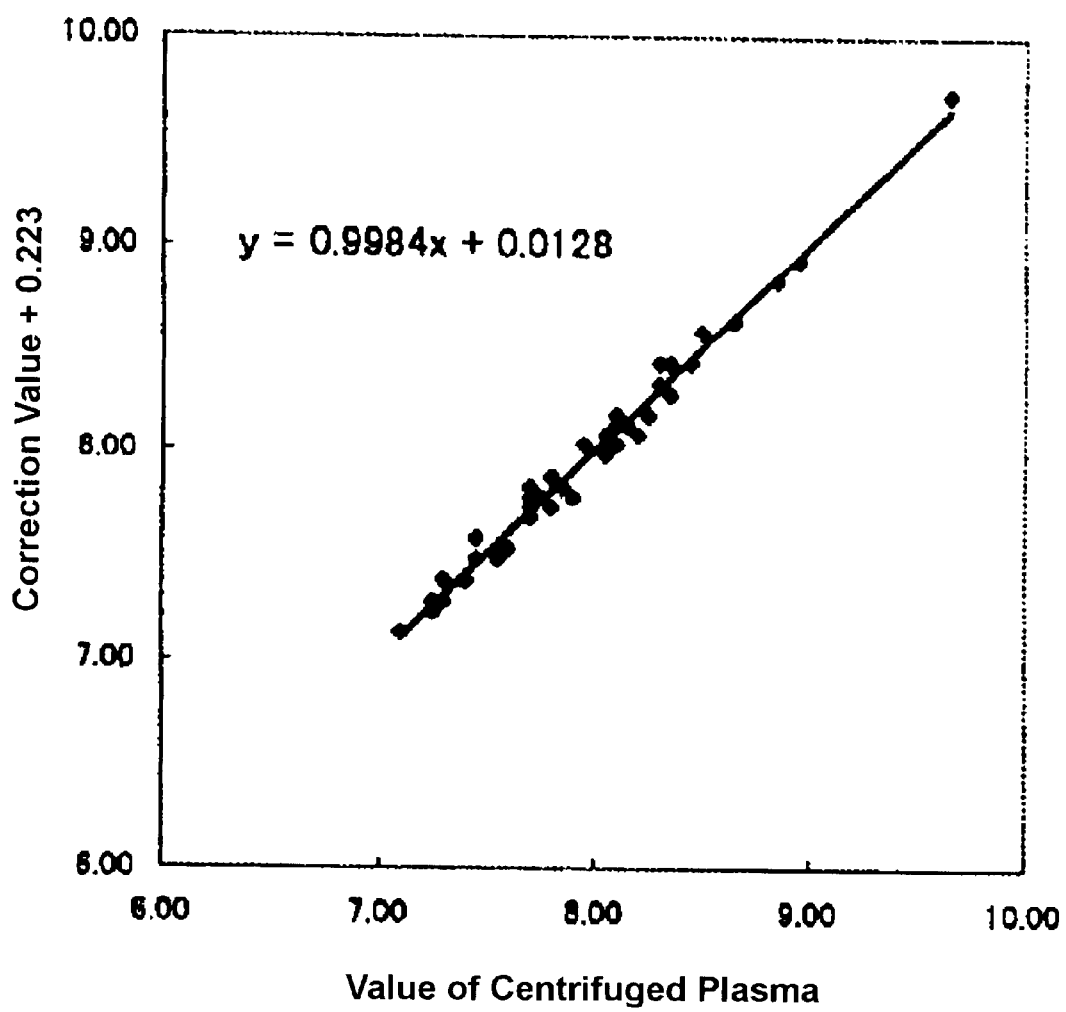
FIG. 4 is a graph showing a correlation after corrected.

The effectiveness of the formula was confirmed by using a plurality of samples (FIG. 4).

Example 3

Similar experiments were carried out, and a and b values were determined as to Ca, ALP (alkaline phosphatase) and $NH_3$, as shown in Table 4.

TABLE 4

| | a | b |
|---|---|---|
| Ca | 1.0 | −0.33 |
| ALP | 0.944 | 0 |
| $NH_3$ | 1.148 | 0 |

The effectiveness of the formulas were also confirmed by using a plurality of samples.

What is claimed is:

1. A method of analyzing a blood component by filtering blood using a glass fiber filter to obtain a plasma or serum sample and measuring the sample, wherein plasma or serum samples obtained by: (1) using a glass fiber filter of the same brand as the glass fiber filter used for filtering blood and (2) a standard method have previously been measured to determine a and b of the formula $$Y = ax + b$$

wherein Y is an analytical value obtained by the standard method and x is an analytical value obtained by using the glass fiber filter of the same brand as the glass fiber filter used for filtering blood, and an analytical value of blood is corrected by using the above formula.

2. The method of claim 1 wherein the standard method is centrifugation.

3. The method of claim 1 wherein the blood component is electrolyte, protein, ammonia-formed nitrogen or enzyme.

4. The method of claim 1 wherein the blood component is a member selected from the group consisting of potassium, sodium, calcium, ammonia, chlorine, total protein and alkaline phosphatase.

5. The method of claim 1 wherein the measuring of the sample is carried out by using a dry analytical element.

6. The method of claim 5 wherein the dry analytical element comprises a porous spreading layer, a hydrophilic polymer layer and a water-impermeable support.

* * * * *